United States Patent [19]

Riedhammer et al.

[11] 4,354,952

[45] Oct. 19, 1982

[54] CONTACT LENS DISINFECTING AND PRESERVING SOLUTION COMPRISING CHLORHEXIDINE AND SALTS THEREOF

[75] Inventors: Thomas M. Riedhammer; Francis X. Smith, both of Rochester, N.Y.

[73] Assignee: Bausch & Lomb Incorporated, Rochester, N.Y.

[21] Appl. No.: 242,964

[22] Filed: Mar. 12, 1981

[51] Int. Cl.³ .......................... C11D 1/84; C11D 3/48
[52] U.S. Cl. .................... 252/106; 252/542; 252/545; 252/546; 252/DIG. 14
[58] Field of Search ....... 252/106, 542, 545, DIG. 14; 424/326

[56] References Cited

U.S. PATENT DOCUMENTS

| | | | |
|---|---|---|---|
| Re. 29,693 | 7/1978 | Phares | 424/326 |
| 3,884,826 | 5/1975 | Phares et al. | 252/106 |
| 3,888,782 | 6/1975 | Boghosian | 252/106 |
| 4,013,576 | 3/1977 | Loeshek | 252/106 |
| 4,046,706 | 9/1977 | Krezanoski | 252/106 |
| 4,104,187 | 8/1978 | Sibley et al. | 252/106 |
| 4,199,567 | 4/1980 | Rankin | 424/173 |
| 4,259,202 | 3/1981 | Tanaka et al. | 252/107 |

*Primary Examiner*—P. E. Willis, Jr.
*Attorney, Agent, or Firm*—Robert M. Phipps

[57] ABSTRACT

A disinfecting and/or preserving solution for contact lenses is disclosed. The disinfecting solution is an aqueous solution containing 0.0035 to 0.04 weight percent of an amphoteric surfactant in combination with 0.0005 to 0.01 weight percent of chlorhexidine and 0.002 to 0.025 weight percent of a non-ionic surfactant, optionally together with up to 0.5 weight percent of thimerosal or other enhancers and optional buffers and the like. The binding (or uptake) of preservative by a hydrophilic soft contact lens is reduced by this invention.

10 Claims, No Drawings

CONTACT LENS DISINFECTING AND PRESERVING SOLUTION COMPRISING CHLORHEXIDINE AND SALTS THEREOF

BACKGROUND

1. Field of the Invention

This invention relates to the use of an amphoteric surfactant in combination with chlorhexidine and a non-ionic surfactant as the active antimicrobial agent in disinfecting and/or preserving solutions for contact lenses.

2. Description of the Prior Art

This invention relates to disinfecting and preserving contact lenses, particularly soft contact lenses. When the term "soft contact lenses" is used herein, it is generally referring to those contact lenses which readily flex under small amounts of force and return to their original shape when released from that force. Typically, soft contact lenses are formulated from poly(hydroxyethyl methacrylate) which has been, in the preferred formulations, crosslinked with ethylene glycol dimethacrylate. For convenience, this polymer is generally known as PHEMA. Soft contact lenses are also made from silicone polymers typically crosslinked with dimethyl polysiloxane. As is known in the art, conventional hard lenses, which cover only the cornea of the eye, usually consist of poly(methylmethacrylate) crosslinked with ethylene glycol dimethacrylate.

Hard contact lenses do not absorb appreciable amounts of water as do some soft contact lenses and thus the use of harsher disinfecting and cleaning agents does not create a problem in the hard contact lenses cleaning area. However, many hard lens disinfecting and preserving solutions contain benzalkonium chloride or chlorobutanol which may render the treated lenses hydrophobic, may not be stable in solution or lack compatibility with certain types of hard lenses, e.g., high silicone content. As is generally known, the users of soft contact lenses are warned against using solutions made for hard contact lenses since the materials in the solutions, as mentioned, may be absorbed or even concentrated by the soft contact lenses and may seriously damage the soft contact lenses or the eye of the user.

U.S. Pat. Reissue No. 29,693, R. E. Phares, Jr., discloses the use of chlorhexidine and its salts, such as chlorhexidine digluconate, as the active agent in soaking and sterilization solutions for soft contact lenses. Preferably the solution is isotonic.

U.S. Pat. No. 3,855,140, M. R. Billany et al, discloses cleaning compositions containing a soluble salt of chlorhexidine, a polyoxyethylene polyoxypropylene block copolymer and an inert diluent or carrier. The compositions are useful as a preoperative scrub in surgical practice.

U.S. Pat. No. 4,013,576, S. Loshaek, discloses an aqueous contact lens treating composition containing a bacteriocide and an amphoteric surfactant as a detergent. The solution provides cleaning, wetting, soaking and cushioning of the lens. Among the useful bacteriocides disclosed are thimerosal, biopal, chlorhexidine and benzalkonium chloride, however, no data is given for chlorhexidine. The amphoteric surfactant has the formula

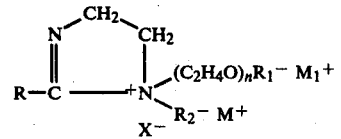

The structure is illustrated in the ionized form as it exists in aqueous media. In this structure, R represents a hydrophobic group and consists of an acid radical such as the fatty acid radicals of $C_6$–$C_{18}$ (coconut oil, lauric acid, capric acid, caprylic and ethylhexoic acid, oleic acid, linoleic acid and stearic acid); $R_2$ is

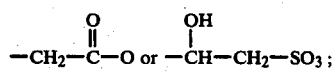

M and $M_1$ are cation salt forming groups, such as hydrogen or alkali metals, X is OH, or the acid group of an anionic surface active agent, e.g., sodium lauryl sulfate or sodium lauryl sulfonate, $R_1$ is H, or

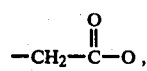

provided, however, when $R_1$ is hydrogen $M_1$ is absent, and n is an integer from 1 to 40. Materials of this type are offered commercially under the tradename "Miranol".

U.S. Pat. No. 4,046,706, J. Z. Krezanoski, discloses an aqueous contact lens cleaning composition comprising (a) a poly(oxyethylene) poly(oxypropylene) block copolymer having a molecular weight between 1900 and 15,500 and a cloud point above 30° C., (b) ethyl or isopropyl alcohol and (c) an amphoteric surfactant having the formula

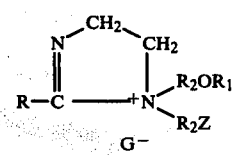

in which R is a $C_6$ to $C_{24}$ hydrocarbon radical, selected from straight or branch chain, saturated or unsaturated, aliphatic hydrocarbon or an alkyl aryl group in which the alkyl group contains at least six carbon atoms, $R_1$ is H, alkali metal, or $CH_2COOM$; $R_2$ is a $C_1$ to $C_4$ alkylene group; Z is

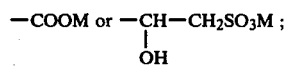

M is alkali metal, H or a nitrogen containing organic base; and G is OH, or a radical comprising the acid group of a $C_6$ to $C_{24}$ anionic surface active sulfate or sulfonate.

Also of interest is U.S. Pat. No. 4,199,567, B. F. Rankin, which discloses chlorhexidine gluconate containing solutions are stabilized against precipitation upon freezing by the addition thereto of certain nonionic surfactants.

SUMMARY OF THE INVENTION

In accordance with this invention, there is provided an aqueous solution for preserving and/or disinfecting contact lenses having as the active antimicrobial agent
 (a) 0.0035 to 0.04 weight percent of an amphoteric surfactant,
 (b) 0.0005 to 0.01 weight percent of chlorhexidine or a water soluble salt thereof, and
 (c) 0.002 to 15 weight percent of a nonionic surfactant.

Typically the solution will be an isotonic solution which may optionally contain enhancing or conditioning agents.

DESCRIPTION OF THE PREFERRED EMBODIMENTS

This invention relates to cleaning and disinfecting solutions (for contact lenses) which contain the antibacterial compound chlorhexidine (1,1'-hexamethylene-bis [5-(p-chlorophenyl) biguanide]) or its water soluble salts. Suitable salts of chlorhexidine are soluble in water at ambient temperature to the extent of at least 0.5 weight percent. These salts include the gluconate, isethionate (2-hydroxyethanesulfonate), formate, acetate, glutamate, succinamate, monodiglycollate, dimethanesulfonate, lactate, diisobutyrate and glucoheptonane. The preferred salt is chlorhexidine gluconate which for convenience will hereafter be referred to as CG.

Applicants have discovered that contact lenses can be effectively disinfected and preserved with aqueous solutions of very dilute chlorhexidine or its salts in combination with certain amphoteric and nonionic surfactants. This is particularly surprising in view of the teachings of U.S. Pat. No. 3,855,140, at Column 1, that amphoteric surfactants are not suitable for use with salts of chlorhexidine because the surfactant destroys the antibacterial activity. Furthermore, U.S. Pat. No. 4,013,576 teaches that when amphoteric surfactants are used in contact lens solutions the bacteriocide must be present in an amount from 0.01 0.15 weight percent. Applicants have found effective, storage-stable contact lens solutions can be obtained with substantially lower amounts of active ingredients than taught by the above patents. Additionally, the lens solutions of this invention reduce the amount of binding (or uptake) of the preservative into hydrophilic soft contact lenses.

The amphoteric charged surfactant molecule consists of a relatively complex organic portion with a net positive or negative charge. The latter charge is balanced by a positive or negative counterion, (e.g., $Na^+$, $Cl^-$) which is not connected to the molecule by a covalent bond but is held in its environment by the attraction between the oppositely charged moieties. In the amphoteric molecule, the complex organic portion referred to above contains both positive and negative charges (at least one of each). As with the singly-charged molecule, electrical neutrality is provided by counterions, both negative and positive counterions being required for the same molecule. The uncharged portion of the amphoteric molecule contains hydrophobic groups (the charged portions usually function as part of the hydrophilic groups) and may contain non-charged (i.e., nonionic) hydrophilic groups.

The preferred amphoteric surfactant molecule of this invention is illustrated by the following chemical structures:

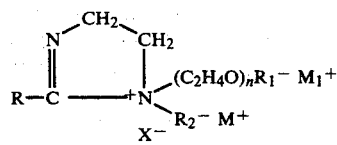

The structure is illustrated in the ionized form as it exists in aqueous media. In this structure, R represents a hydrophobic group and consists of an acid radical such as the fatty acid radicals of $C_6$-$C_{18}$, e.g., coconut oil which is a mixture of lauric, myristic, oleic, stearic, palmitic, and other similar acids, lauric acid, capric acid, caprylic and ethylhexoic acid, oleic acid, linoleic acid and stearic acid; $R_2$ is

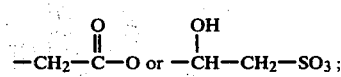

M and $M_1$ are cation salt forming groups, such as hydrogen or alkali metals, X is OH, or the acid group of an anionic surface active agent, e.g., sodium lauryl sulfate or sodium lauryl sulfonate, $R_1$ is H or

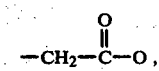

provided, however, when $R_1$ is hydrogen, $M_1$ is absent and n is an integer from 1 to 40. Materials of this type are offered commercially under the tradename "Miranol". Typical examples of ionized amphoteric salts (commercial tradenames Miranol 2MCA and C2M respectively) are shown below:

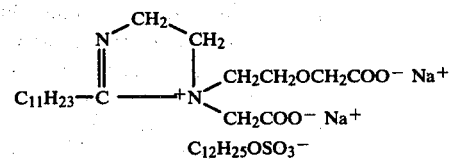

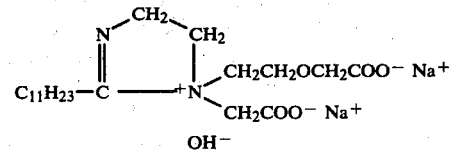

Broadly, these compounds can be monocarboxylate, dicarboxylates or sulfonates. The counterions in the first example are $Na^+$ and $C_{12}H_{25}OSO_3^-$ and in the second example $Na^+$ and $OH^-$.

Another class of amphoteric surfactants is given by the following chemical structure in the ionized form:

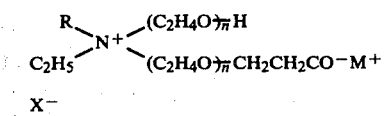

where R is a hydrophobe radical such as methyl octadecyl, methyldodecyl, methyloctadecenyl, etc.; M is an alkali metal, such as Na, K, etc.; X is the negative part of an agent, such as $CH_3OSO_3$, $C_2H_5OSO_3$, Cl, Br, etc., n is an integer from 1 to 40. Materials of this type are available commercially under the tradename Sanac. This molecule has a nonionic functionality, $(C_2H_4O)_nH$. Specific examples are [2-(2-carboxyethyl) ethyl][2-(2-hydroxyethyl) ethyl] methyloctadecylammonium methyl sulfate, potassium salt; [2-2-carboxyethyoxy) ethyl] [2-(2-hydroxyethoxy) ethyl] methyloctadecenylammonium methyl sulfate, potassium salt; and [2-2-carboxyethyoxy) ethyl] [2-(2-hydroxyethoxy) ethyl] methyldodecylammonium methyl sulfate, potassium salt.

Another class of amphoteric surfactants may be exemplified by the following chemical structure, in the ionized form:

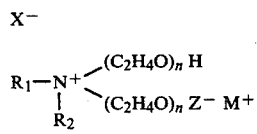

where $R_1$ is a fatty acid radical or other hydrophobe radical, $R^2$ is an alkyl or substituted alkyl radical, Z is a sulfate or sulfonic group, e.g., $-SO_4$, $-CH_2CH_2SO_3$; M is an alkali metal such as Na or K; X is the negative radical from a quaternizing reagent such as $CH_3OSO_3$, $C_2H_5OSO_3$, Cl, Br, etc.

Yet another class of amphoteric surfactants may be exemplified by the following chemical structure in the ionized form:

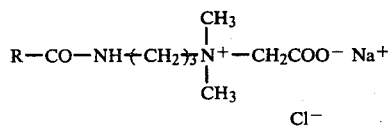

wherein R is alkylene having 12 to 13 atoms and R—CO— taken together as the acid radical such as coconut acid. Materials of this type are exemplified by cocamidopropyl betaine commercially available under the tradename Amphosol CA.

The particular amphoteric surfactant is not the subject of the present invention, but rather the use of such a surfactant in contact lens formulations which is to be illustrated in the following examples. The surfactant purity must be adequate so that impurities introduced during synthesis and not removed, do not react adversely or antagonistically with antibacterial agents or other ingredients.

The contact lens solution contains from 0.0035 to 0.04 weight percent and preferably from 0.007 to 0.02 weight percent of the amphoteric surfactant.

The third component of the active antimicrobial agent of this invention is a neutral (nonionic) surfactant present in an amount from 0.002 to 0.025 weight percent when the solution is a preserving or disinfecting solution. When the contact lens solution is also to be used as a cleaner, the concentration of nonionic surfactant may be increased up to 15 weight percent of the solution and preferably about one weight percent. The selected nonionic surfactant will be soluble in the lens solution, non-irritating to the eye and have a hydrophile lipophile balance (HLB) number of 12.4 to 18.8 and preferably 15.9 to 17.0. Satisfactory nonionic surfactants for this invention include polyethylene glycol esters of fatty acids (e.g., coconut, polysorbate), polyoxyethylene or polyoxypropylene ethers of higher alkanes ($C_{12}-C_{18}$). Examples of the preferred class are polysorbate (20) (tradename Tween 20), polyoxyethylene (23) lauryl ether (tradename Brij 35), polyoxyethylene (40) stearate (tradename Myrj 52) and polyoxyethylene (25) propylene glycol stearate (tradename Atlas G 2612). Other nonionic surfactants suitable for use in this invention can be readily ascertained, in view of the foregoing description, from McCutcheons's Detergents and Emulsifiers, North American Edition, McCutcheon Division, MC Publishing Co., Glen Rock, NJ 07452, U.S.A., 1980.

The antimicrobial effect of the foregoing three component system can be enhanced or increased by the use of an enhancer. An enhancer can be present in an amount from zero to about 0.5 weight percent and preferably from about 0.0001 to about 0.1 weight percent. Suitable enhancers are selected from the group which includes thimerosal, sorbic acid, phenylmercuric salts (e.g., nitrate, borate, acetate or chloride), ethylenediaminetetraacetic acid (EDTA) and its salts and mixtures of the foregoing enhancers. A particularly preferred enhancer is thimerosal used in an amount from 0.0001 to about 0.002 weight percent.

A typical composition of the present invention may contain, in addition to the active ingredients described earlier, buffers, cleaners, stabilizers and isotonic agents which aid in making the ophthalmic composition more comfortable to the user. These additional materials must be non-toxic and must not distort the lens.

Suitable buffers include sodium or potassium citrate, citric acid, boric acid, sodium bicarbonate and various mixed phosphate buffers including combinations of $Na_2HPO_4$, $NaH_2PO_4$ and $KH_2PO_4$. Generally, buffers may be used in amounts ranging from about 0.05 to 2.5 and preferably 0.1 to 1.5% (w/v).

The treating solution for contact lenses is typically maintained at an osmotic pressure similar to that of physiological saline, i.e., substantially isotonic, or equivalent to 0.9% saline, or with suitable agents alone or in combination to render the solution substantially isotonic. Hypotonic solution, e.g., tap water, may cause a lens to adhere tightly to the cornea while hypertonic solutions (excess saline) may result in stinging, lacrimation and a red eye.

The method of use of the solution comprises having the wearer of the contact lenses remove the lenses from the eyes. Then the lenses are rubbed with preserved cleaning solution, rinsed with preserved saline solution and placed in a suitable container with a sufficient amount of the composition of the instant invention to cover the lenses. The lenses are allowed to soak preferably for a period of from about 4 hours to about 12 hours at room temperature. The lenses are then removed from the solution, washed with saline solution and then replaced on the eyes.

The following examples are illustrative only and should not be construed as limiting the invention. All parts and percentages referred to herein are on a weight per volume basis. The saline solution used in the examples is an isotonic, buffered saline solution unless otherwise specified.

EXAMPLE I

Preserved Saline Solution

To an isotonic saline solution is added 0.001 percent CG, 0.01 percent 2-cocoyl-1-(sodium carboxymethyl)-1-[(sodium carboxymethoxy) ethyl]-2-imidazolinium hydroxide (as the 38% active material available under the tradename Miranol C2M), 0.015 percent polyoxyethylene (28) lauryl ether (tradename Brij 35) and 0.1 percent of disodium EDTA. The solution is exposed to approximately 1,000,000 microorganisms per ml of the indicated organism. The solution is considered effective if the concentration of *Pseudomonas aeruginosa* or *Staphylococcus aureus* is reduced to less than 0.1% of the initial concentration within 14 days and *Apergillus niger* is maintained at its original level. The solution is considered effective.

EXAMPLE II

Disinfecting Solution

Isotonic disinfecting solutions for soft contact lenses are prepared by mixing together 0.005 weight percent CG and specified amounts of Miranol C2M amphoteric surfactant (38 percent active material) and Atlas G 2612 nonionic surfactant. When indicated, the solutions also contain 0.002 weight percent of thimerosal. The solution is exposed to approximately 1,000,000 microorganisms per ml for six hours. The solution is considered effective if there is at least a 99.9% reduction of the viable microorganism. The solutions are prepared and evaluated as indicated in Table I below.

TABLE I

| SOLUTION | AMPHOTERIC WT. PERCENT | ENHANCER | NONIONIC WT. PERCENT | EXPOSURE RESULT[1] | | | |
|---|---|---|---|---|---|---|---|
| | | | | S. epidermidis | C. albicans | A. fumigatus | A. niger |
| A | 0.005 | Yes | 0.015 | ++ | ++ | ++ | ++ |
| B | 0.05 | Yes | 0.015 | ++ | ++ | ++ | ++ |
| C | 0.10 | Yes | 0.015 | ++ | + | ++ | ++ |
| D | 0.20 | Yes | — | NE | ++ | ++ | ++ |
| E | 0.05 | Yes | 0.01 | ++ | ++ | + | ++ |
| F | 0.05 | No | 0.01 | ++ | NE | NE | * |
| G | 0.10 | No | 0.01 | + | NE | NE | * |
| H | SALINE CONTROL | | — | NE | NE | NE | NE |

[1] ++ = Effective
+ = Marginal
NE = Not Effective
* = Not Tested

EXAMPLE III

Disinfecting Solutions

Two isotonic solutions with 0.005 weight percent CG and 0.05 weight percent Miranol C2M amphoteric surfactant, one containing 0.005 weight percent Brij 35 nonionic surfactant and the other 0.005 weight percent Myrj 52 nonionic surfactant are evaluated in a disinfecting regimen for soft contact lenses. Both solutions are found to be effective since the regimen completely removes from the lenses or kills the six pathogenic challenge organisms recommended by the U.S. Food and Drug Administration.

EXAMPLE IV

Comparative-Solubility of Complex

Isotonic solutions of amphoteric (Miranol C2M) surfactant and CG are prepared and then set aside for a short period of time. Then the turbidity of the solution is noted. A turbid solution is not satisfactory for contact lens disinfecting solutions. The results are tabulated in Table II. Additional isotonic solutions of the foregoing amphoteric surfactant and CG are prepared which also contain a nonionic surfactant (Atlas G 2162).

These solutions are also observed for turbidity and the results are a part of Table II below.

TABLE II

| SOLUTION | AMPHOTERIC SURFACTANT (WEIGHT PERCENT) | CG (WEIGHT PERCENT) | NONIONIC SURFACTANT (WT. PERCENT) | APPEARANCE |
|---|---|---|---|---|
| A | 0.05 | 0.005 | — | Turbid |
| B | 0.10 | 0.005 | — | Turbid |
| C | 0.05 | 0.0075 | — | Turbid |
| D | 0.10 | 0.015 | — | Turbid |
| E | 0.30 | 0.005 | — | Clear |
| F | 0.02 | 0.005 | 0.001 | Turbid |
| G | 0.02 | 0.005 | 0.002 | Clear |
| H | 0.02 | 0.005 | 0.003 | Clear |
| I | 0.10 | 0.005 | 0.020 | Clear |
| J | 0.10 | 0.005 | 0.025 | Clear |

EXAMPLE V

Preserved Cleaner

A surfactant cleaner for lens cleaning containing 0.1% of a neutral polyoxyethylene fatty acid nonionic surfactant (sold under the trademark Myrj 52 by Atlas Powder Co.) is added to an isotonic solution. To the cleaner is added 0.005 weight percent Miranol 2MCA (approximately 38 percent active material) and 0.005 weight percent chlorhexidine acetate. The standard of effectiveness against *P. aeruginosa* is determined as in Example I. The solution is considered effective against *Candida albicans* (ATCC No. 10231) if its concentration remains at or below the initial concentration of 1,000,000 microorganisms per ml for 14 days. No enhancer is added to the cleaner. The cleaner is considered effective.

EXAMPLE VI

Preservative Binding

The binding or absorption of preservative from a disinfecting solution by a hydrophilic soft contact lens is of great concern since many chemicals otherwise suitable for preservative use are injurious to the cornea. In this example, the binding of CG from various solutions is compared. To an isotonic solution having 0.005 weight percent CG is added the indicated amount of amphoteric (Miranol C2M) and nonionic (Atlas G 2162) surfactants. A hydrophilic soft contact lens (polyhydroxyethylmethacrylate) is exposed in 100 ml of disinfecting solution for 48 hours. The lens is then analyzed by ultraviolet spectrometry for CG absorption. CG has a maximum peak at 255 nm. A 25 ml portion of the remaining test solution is chemically analyzed for amount of CG remaining. The results are tabulated in Table III which follows:

TABLE III

| SOLUTION | AMOUNT AMPHOTERIC (WT. PERCENT) | AMOUNT NONIONIC (WT. PERCENT) | BINDING $(UV)^a$ | CG ABSORPTION (PERCENT) |
|---|---|---|---|---|
| A | — | — | Y | 15 |
| B | — | 0.1 | Y | *b |
| C | 0.05 | — | $S^c$ | * |
| D | 0.05 | 0.01 | S | * |
| E | 0.05 | 0.015 | S | 3 |
| F | 0.3 | 0.01 | $N^d$ | * |

$^a$binding Y - strong binding S - slight binding N - none
*not evaluated
$^c$solution was turbid
$^d$insufficient antimicrobial activity The preceding examples show the unique three-component antimicrobial system of this invention as an effective eye contact lens disinfectant at substantially lower use levels than taught by the prior art.

These examples also demonstrate the criticality of the ratio between the three components in balancing between microbial effectiveness and binding of the microbial agent. Minimum binding is obtained at a ratio of 20 parts amphoteric to one part of chlorhexidine. Maximum antimicrobial activity is achieved by ratio of one part amphoteric to one part chlordhexidine. Optimum properties are obtained at a ratio of 10 parts amphoteric: one part chlorhexidine: 2 parts of nonionic.

The foregoing examples and methods have been described in the foregoing specification for the purpose of illustration and not limitation. Many other modifications and ramifications will naturally suggest themselves to those skilled in the art based on this disclosure. These are intended to be comprehended as within the scope of this invention.

The embodiments of the invention in which an exclusive property or privilege is claimed are defined as follows:

1. An aqueous solution for preserving and/or disinfecting soft contact lenses having as the active antimicrobial agent a combination 0.0005 to 0.01 weight percent of said composition chlorhexidine or salt thereof, 0.0035 to 0.04 weight percent of said composition of amphoteric surfactant and 0.002 to 15 weight percent of said composition of a nonionic surfactant having a hydrophiliclipophile balance between 12.4 and 18.8, said amphoteric surfactant being selected from the group consisting of:

$$\begin{array}{c} \phantom{R-C} \overset{CH_2}{\underset{\phantom{x}}{N}} \overset{}{\underset{CH_2}{\diagdown}} \\ R-C \underset{\phantom{x}}{\overset{\|}{\phantom{-}}} \phantom{x} \underset{X^-}{\overset{+}{N}} \overset{(C_2H_4O)_n R_1^- M_1^+}{\underset{R_2^- M^+}{\diagup}} \end{array} \quad (1)$$

wherein

R is a fatty acid radical having 6 to 18 carbon atoms
$R_1$ is H or $-CH_2C(O)O$ provided that when $R_1$ is H then $M_1$ is absent
$R_2$ is $-CH_2C(O)O$ or $CH(OH)CH_2SO_3$
M and $M_1$ are cation salt forming groups
X is OH or the acid group of an anionic surface active agent
n is an integer from 1 to 40;

$$\begin{array}{c} R \diagdown \underset{C_2H_5}{\overset{+}{N}} \overset{(C_2H_4O)_n H}{\underset{(C_2H_4O)_{\overline{n}} CH_2CH_2CO^- M^+}{\diagup}} \\ X^- \end{array} \quad (2)$$

wherein
R is a hydrophobe radical
M is an alkali metal
X is selected from $CH_3OSO$, $C_2H_5OSO_3$, Cl or Br
n is an integer from 1 to 40;

$$\begin{array}{c} X^- \\ R_1 - \underset{\underset{R_2}{\mid}}{\overset{+}{N}} \overset{(C_2H_4O)_n H}{\underset{(C_2H_4O)_n Z^- M^+}{\diagup}} \end{array} \quad (3)$$

wherein
$R_1$ is a fatty acid or hydrophobe radical
$R_2$ is alkyl or substituted alkyl
Z is sulfate or sulfonic
M is alkali metal
X is $CH_3OSO_3$, $C_2H_5OSO_3$, Cl or Br; or $$R-CO-NH \overset{}{\leftarrow} CH_2 \overset{}{\rightarrow_3} \underset{\underset{CH_3}{\mid}}{\overset{\overset{CH_3}{\mid}}{N^+}} -CH_2COO^- Na^+ \qquad (4)$$
$$\phantom{R-CO-NH(CH_2)_3N^+-CH_2COO^-Na^+} Cl^-$$

wherein
R is alkylene of 12–13 carbon atoms,
said nonionic surfactant being selected from polyethylene glycol esters of fatty acids, polyoxyethylene ethers of higher alkanes and polyoxypropylene ethers of higher alkanes.

2. The composition of claim 1 wherein the amount of amphoteric surfactant is from 0.007 to 0.02 weight percent, the chlorhexidine or salt thereof is from 0.002 to 0.01 weight percent and the nonionic surfactant is from 0.002 to 0.025 weight percent.

3. The composition of claim 1 wherein an enhancing agent is present in an amount up to 0.5 weight percent and the chlorhexidine salt is chlorhexidine gluconate, said enhancing agent being selected from the group consisting of thimerosal, sorbic acid, phenylmercuric salts, ethylenediaminetetracetic acid and its salts and mixtures thereof.

4. The composition of claim 3 wherein the enhancer is thimerosal.

5. The composition of claim 3 wherein the enchancing agent is the disodium salt of ethylenediaminetetraacetic acid.

6. The composition of claim 3 wherein the enhancer is present in an amount from about 0.0001 to about 0.1 weight percent.

7. A method of disinfecting contact lenses comprising contacting the lenses for a sufficient time to disinfect the lenses with the aqueous solution of claim 1.

8. A method of inhibiting microorganism growth in a solution for use with contact lenses comprising treating the lenses with the aqueous solution of claim 1.

9. A method of cleaning contact lenses comprising rubbing the lens with the preserved cleaning solution of claim 1 and rinsing with a preserved saline solution.

10. The method of claim 9 wherein the contact lens is a soft contact lens.

* * * * *